United States Patent
Wendland et al.

(10) Patent No.: US 10,058,844 B2
(45) Date of Patent: Aug. 28, 2018

(54) DIVINYLBENZENE/MALEIC ANHYDRIDE POLYMERIC SORBENTS FOR CARBON DIOXIDE

(71) Applicant: 3M INNOVATIVE PROPERTIES COMPANY, St. Paul, MN (US)

(72) Inventors: Michael S. Wendland, North St. Paul, MN (US); Michael W. Kobe, Lake Elmo, MN (US)

(73) Assignee: 3M INNOVATIVE PROPERTIES COMPANY, Saint Paul, MN (US)

( * ) Notice: Subject to any disclaimer, the term of this patent is extended or adjusted under 35 U.S.C. 154(b) by 0 days.

(21) Appl. No.: 15/580,733

(22) PCT Filed: Jun. 16, 2016

(86) PCT No.: PCT/US2016/037747
§ 371 (c)(1),
(2) Date: Dec. 8, 2017

(87) PCT Pub. No.: WO2016/205444
PCT Pub. Date: Dec. 22, 2016

(65) Prior Publication Data
US 2018/0147555 A1    May 31, 2018

Related U.S. Application Data

(60) Provisional application No. 62/182,057, filed on Jun. 19, 2015.

(51) Int. Cl.
| | |
|---|---|
| *B01D 53/02* | (2006.01) |
| *C07C 7/12* | (2006.01) |
| *B01J 20/26* | (2006.01) |
| *B01J 20/28* | (2006.01) |
| *B01J 20/30* | (2006.01) |
| *C08F 212/36* | (2006.01) |
| *C10L 3/10* | (2006.01) |

(52) U.S. Cl.
CPC ............ *B01J 20/261* (2013.01); *B01D 53/02* (2013.01); *B01J 20/2808* (2013.01); *B01J 20/28061* (2013.01); *B01J 20/28083* (2013.01); *B01J 20/28092* (2013.01); *B01J 20/3085* (2013.01); *C07C 7/12* (2013.01); *C08F 212/36* (2013.01); *C10L 3/104* (2013.01); *B01D 2253/202* (2013.01); *B01D 2253/306* (2013.01); *B01D 2256/16* (2013.01); *B01D 2256/245* (2013.01); *B01D 2257/504* (2013.01); *C08F 2800/20* (2013.01); *C10L 2290/542* (2013.01)

(58) Field of Classification Search
None
See application file for complete search history.

(56) References Cited

U.S. PATENT DOCUMENTS

| | | | |
|---|---|---|---|
| 4,273,751 A | 6/1981 | Sinha | |
| 4,677,096 A | 6/1987 | Van der Smissen | |
| 6,930,219 B2 | 8/2005 | Shan | |
| 7,559,981 B2 | 7/2009 | Friday | |
| 8,470,074 B2 * | 6/2013 | Baugh ................ | B01D 53/1475 423/230 |
| 9,776,131 B2 * | 10/2017 | Eisenberger ........... | B01D 53/62 |
| 2009/0060809 A1 | 3/2009 | Shioya | |
| 2014/0186250 A1 | 7/2014 | Levan | |
| 2017/0333870 A1 | 11/2017 | Wendland | |

FOREIGN PATENT DOCUMENTS

| | | |
|---|---|---|
| WO | WO 2011/035195 | 3/2011 |
| WO | WO 2015/095110 | 6/2015 |
| WO | WO 2015/095115 | 6/2015 |
| WO | WO 2016/205083 | 12/2016 |
| WO | WO 2017/106434 | 6/2017 |
| WO | WO 2017/106438 | 6/2017 |

OTHER PUBLICATIONS

AREAN, "Carbon Dioxide and Nitrogen Adsorption on Porous Copolymers of Divinylbenzene and Acrylic Acid", Adsorption, Apr. 2013, vol. 19, Nos. 2-4, pp. 367-372.
BOTTCHER, "Silica Sol-Gel Glasses with Embedded Organic Liquids", Advanced Materials, Feb. 1999, vol. 11, No. 2, pp. 138-141.
KALIVA, "Microporous Polystyrene Particles for Selective Carbon Dioxide Capture", Langmuir, Feb. 7, 2012, vol. 28, No. 5, pp. 2690-2695.
NIU, "Highly Dispersed Ru on K-Doped Meso-Macroporous $SiO_2$ for the Preferential, Oxidation of CO in $H_2$-rich Gases", International Journal of Hydrogen Energy, Aug. 22, 2014, vol. 39, No. 25, pp. 13800-13807.
SONG, "Coordination of Metal Cations with Amino-Functionalized MCM-41 for Adsorptive Desulfurization", Advanced Materials Research, 2014, vols. 926-930, pp. 4222-4225.
WOODWARD, "Swellable, Water- and Acid-Tolerant Polymer Sponges for Chemoselective Carbon Dioxide Capture", Journal of the American Chemical Society, Jun. 25, 2014, vol. 136, No. 25, pp. 9028-9035.
YANG, "A Pervaporation Study of Ammonia Solutions Using Molecular Sieve Silica Membranes", Membranes, Mar. 2014, vol. 4, No. 1, pp. 40-54.
International Search Report for PCT International Application No. PCT/US2016/037747, dated Sep. 15, 2016, 4 pages.

* cited by examiner

*Primary Examiner* — Tam M Nguyen
(74) *Attorney, Agent, or Firm* — Jean A. Lown (57) ABSTRACT

Methods of sorbing carbon dioxide on porous divinylbenzene/maleic anhydride polymeric sorbents are provided. Additionally, compositions resulting from sorbing carbon dioxide on porous divinylbenzene/maleic anhydride polymeric sorbents are provided. The porous polymeric sorbents typically have micropores, mesopores, or a combination thereof and can selectively remove carbon dioxide from other gases such as methane.

15 Claims, 2 Drawing Sheets

DIVINYLBENZENE/MALEIC ANHYDRIDE POLYMERIC SORBENTS FOR CARBON DIOXIDE

CROSS REFERENCE TO RELATED APPLICATIONS

This application is a national stage filing under 35 U.S.C. 371 of PCT/US2016/037747, filed Jun. 16, 2016, which claims the benefit of U.S. Provisional Application No. 62/182,057, filed Jun. 19, 2015, the disclosure of which is incorporated by reference in its/their entirety herein.

TECHNICAL FIELD

Methods of sorbing carbon dioxide and compositions resulting from sorbing carbon dioxide on porous divinylbenzene/maleic anhydride polymeric sorbents are provided.

BACKGROUND

The production of energy from coal and natural gas requires technologies to remove carbon dioxide ($CO_2$), which is a gaseous impurity in both processes. The low cost and global abundance of both coal and natural gas all but ensures the continued use of these two natural resources for energy generation for many years to come. Efforts to develop technologies to improve the removal of unwanted $CO_2$ through the development of selective, high capacity sorbents for $CO_2$ are needed.

To generate energy from coal, integrated gasification combined cycle (IGCC) power plants make use of the water-gas shift reaction. Coal is burned and the carbon monoxide produced is then reacted with water in a reactor containing a catalyst to perform the water-gas shift reaction. This reaction converts water and carbon monoxide to carbon dioxide and hydrogen. The $CO_2/H_2$ gas stream produced (called synthetic gas or syngas) typically contains about 35-40 mole percent $CO_2$. An important step in electricity generation at IGCC power plants is the removal of the carbon dioxide generated by the water-gas shift reaction to produce fuel grade or even higher purity hydrogen. The hydrogen is subsequently used to power a combined cycle turbine that produces electricity.

The most widely used method to remove the $CO_2$ from $H_2$ is a pressure swing adsorption cycle with the sorbent being a physical solvent. In a pressure swing adsorption cycle, a $CO_2/H_2$ gas stream at high pressure (e.g., 20-45 bar) is passed through the physical solvent resulting in a purified $H_2$ stream exiting the sorbent vessel. The adsorption portion of the cycle is stopped prior to breakthrough of a targeted level of $CO_2$. A desorption step is then performed to regenerate the physical solvent.

Physical solvents separate $CO_2$ from other gases based on a difference in solubility. Because there are only weak interactions between the $CO_2$ and the physical solvent, the $CO_2$ can be easily removed from the physical solvent by reducing the pressure. While there are several different physical solvents in use today, polyethylene glycol dimethyl ether (available under the trade designation SELEXOL) is the most commonly used. While the adsorption selectivity for $CO_2$ is high, the solubility of $CO_2$ in SELEXOL at 20 bar and 25° C. is only about 9.6 weight percent. Although the solubility amount can vary depending on the temperature and pressure used in the process, the ability to capture a higher percentage of $CO_2$ per mass of sorbent while maintaining selectivity over other gases such as hydrogen would be highly advantageous.

Natural gas production requires an extensive set of processes to purify the natural gas to a useable fuel. Typical impurities include acid gases (such as hydrogen sulfide and sulfur dioxide), water, and carbon dioxide. Carbon dioxide is typically present in natural gas at a level close to 5 volume percent. While the most common method to remove $CO_2$ from methane is a pressure swing adsorption cycle, the low partial pressure of the $CO_2$ in the mixture makes the removal of $CO_2$ with physical solvents impractical. A stronger interaction between the $CO_2$ and solvent is required. As such, chemical solvents are typically used. The most widely used chemical solvent is an aqueous solution of ethanol amine. In a single pressure swing adsorption cycle, ethanol amine can separate/capture about 5 percent of its mass in $CO_2$. While the strong interaction of the $CO_2$ with the chemical solvent allows for the efficient removal of the $CO_2$ from the gas stream, regeneration of the chemical solvent requires heating. This heating step tends to render the overall process energetically expensive.

Polymeric materials prepared from divinylbenzene and maleic anhydride have been known for many years. Many of these polymeric materials are prepared by a process called macroreticulation, which refers to a process of making polymeric beads using suspension polymerization. These processes involve forming droplets of an organic phase suspended in an aqueous phase. The suspended organic phase includes the monomers and an optional porogen. The maleic anhydride content in the final copolymer has been low, however, because this monomer tends to undergo hydrolysis and leave the organic phase. Attempts to reduce the hydrolysis reaction have included replacing the aqueous phase with glycerol or other polar solvents. Macroporous copolymers have been prepared.

SUMMARY

Methods of sorbing carbon dioxide on porous divinylbenzene/maleic anhydride polymeric sorbents are provided. Additionally, compositions resulting from sorbing carbon dioxide on porous divinylbenzene/maleic anhydride polymeric sorbents are provided. The porous polymeric sorbents typically have micropores, mesopores, or a combination thereof and can selectively remove carbon dioxide from other gases such as methane or hydrogen.

In a first aspect, a method of sorbing carbon dioxide on a porous polymeric sorbent is provided. The method includes providing a polymeric sorbent having a BET specific surface area equal to at least 300 $m^2$/gram. The porous polymeric sorbent contains (a) 8 to 52 weight percent of a first monomeric unit of Formula (I), (b) 48 to 85 weight percent of a second monomeric unit of Formula (II), (II)

and (c) 0 to 20 weight percent of a third monomeric unit of Formula (III) wherein $R^1$ is hydrogen or alkyl.

(III)

Each weight percent value is based on a total weight of the porous polymeric sorbent. Each asterisk (*) (here and throughout) denotes the location of attachment of the monomeric unit to another monomeric unit or to a terminal group. The method further includes exposing the porous polymeric sorbent to a gas mixture containing carbon dioxide and sorbing carbon dioxide on the porous polymeric sorbent.

In a second aspect, a composition is provided that includes (a) a porous polymeric sorbent and (b) carbon dioxide sorbed on the porous polymeric sorbent. The porous polymeric sorbent comprises (i) 8 to 52 weight percent of a first monomeric unit of Formula (I), (I)

(ii) 48 to 85 weight percent of a second monomeric unit of Formula (II), and (II)

(iii) 0 to 20 weight percent of a third monomeric unit of Formula (III) wherein $R^1$ is hydrogen or alkyl.

(III)

Each weight percent value is based on a total weight of the porous polymeric sorbent. Each asterisk (*) (here and throughout) denotes the location of attachment of the monomeric unit to another monomeric unit or to a terminal group.

DETAILED DESCRIPTION

Methods of sorbing carbon dioxide on porous divinylbenzene/maleic anhydride polymeric sorbents are provided. Additionally, compositions resulting from sorbing carbon dioxide on porous divinylbenzene/maleic anhydride polymeric sorbents are provided. The porous polymeric sorbents typically have micropores, mesopores, or a combination thereof and can selectively remove carbon dioxide from other gases such as methane or hydrogen.

The terms "a", "an", and "the" are used interchangeably with "at least one" to mean one or more of the elements being described.

The term "and/or" means either or both. For example "A and/or B" means only A, only B, or both A and B.

The terms "polymer" and "polymeric material" are used interchangeably and refer to materials formed by reacting one or more monomers. The terms include homopolymers, copolymers, terpolymers, or the like. Likewise, the terms "polymerize" and "polymerizing" refer to the process of making a polymeric material that can be a homopolymer, copolymer, terpolymer, or the like.

The terms "polymeric sorbent" and "porous polymeric sorbent" are used interchangeably to refer to a polymeric material that is porous and that can sorb gaseous substances such as, for example, carbon dioxide. Porous materials such as the polymeric sorbents can be characterized based on the size of their pores. The term "micropores" refers to pores having a diameter less than 2 nanometers. The term "mesopores" refers to pores having a diameter in a range of 2 to 50 nanometers. The term "macropores" refers to pores having a diameter greater than 50 nanometers. The porosity of a polymeric sorbent can be characterized from an adsorption isotherm of an inert gas such as nitrogen or argon by the porous material under cryogenic conditions (i.e., liquid nitrogen at 77° K). The adsorption isotherm is typically obtained by measuring adsorption of the inert gas such as argon by the porous polymeric sorbent at multiple relative pressures in a range of about $10^{-6}$ to about 0.98±0.01. The isotherms are then analyzed using various methods such as BET method (Brunauer-Emmett-Teller method) to calculate specific surface areas and density functional theory (DFT) to characterize the porosity and the pore size distribution.

The term "sorbing" and similar words such as "sorbs" and "sorbed" refer to the addition of a first substance (e.g., a gas such as carbon dioxide, hydrogen, or methane) to a second substance (e.g., a polymeric material such as the porous polymeric sorbent) by adsorbing, absorbing, or both. Likewise, the term "sorbent" refers to a second substance that sorbs a first substance by adsorbing, absorbing, or both.

The term "surface area" refers to the total area of a surface of a material including the internal surfaces of accessible pores. The surface area is typically calculated from adsorption isotherms obtained by measuring the amount of an inert gas such as nitrogen or argon that adsorbs on the surface of a material under cryogenic conditions (i.e., liquid nitrogen 77° K) over a range of relative pressures. The term "BET specific surface area" is the surface area per gram of a material that is typically calculated from adsorption isotherm data of the inert gas over a relative pressure range of 0.05 to 0.3 using the BET method.

The term "monomer mixture" refers to that portion of a polymerizable composition that includes the monomers. More specifically, the monomer mixture includes at least divinylbenzene and maleic anhydride. The term "polymerizable composition" includes all materials included in the reaction mixture used to form the polymeric material. The polymerizable composition includes, for example, the monomer mixture, the organic solvent, the initiator, and other optional components. Some of the components in the polymerizable composition such as the organic solvent may not undergo a chemical reaction but can influence the chemical reaction and the resulting polymeric material.

The term "divinylbenzene/maleic anhydride polymeric material" refers to a polymeric material prepared from divinylbenzene, maleic anhydride, and optionally a styrene-type monomer. Styrene-type monomers are often present as impurities in divinylbenzene.

The term "styrene-type monomer" refers to styrene, an alkyl substituted styrene (e.g., ethyl styrene), or mixtures thereof. These monomers are often present in divinylbenzene as impurities.

The term "room temperature" refers to a temperature in a range of 20° C. to 30° C., in a range of 20° C. to 25° C., in a range close to 25° C., or 25° C.

A method of sorbing carbon dioxide is provided. The carbon dioxide is sorbed on a porous polymeric sorbent that includes (a) 8 to 52 weight percent of a first monomeric unit of Formula (I),

(I)

(b) 48 to 85 weight percent of a second monomeric unit of Formula (II), (II)

and (c) 0 to 20 weight percent of a third monomeric unit of Formula (III) wherein $R^1$ is hydrogen or alkyl.

(III)

Each weight percent value is based on a total weight of the porous polymeric sorbent. Each asterisk (*) denotes the location of an attachment site of the monomeric unit to another monomeric unit or to a terminal group. The carbon dioxide can be sorbed at room temperature or at any desired temperature such as in a range of −30° C. to 150° C. or in a range of −20° C. to 50° C.

Stated differently, the porous polymeric sorbent is a divinylbenzene/maleic anhydride polymeric material that is synthesized from a monomer mixture of maleic anhydride, divinylbenzene, and an optional styrene-type monomer. Maleic acid results in a monomeric unit of Formula (I), divinylbenzene results in a monomeric unit of Formula (II), and styrene-type monomers result in monomeric units of Formula (III) in the porous polymeric sorbent. More specifically, the monomer mixture includes 1) 8 to 52 weight percent maleic anhydride, 2) 48 to 85 weight percent divinylbenzene, and 3) 0 to 20 weight percent of a styrene-type monomer, wherein the styrene-type monomer is styrene, an alkyl substituted styrene, or a combination thereof. In some instances, the monomer mixture includes 1) 8 to 40 weight percent maleic anhydride, 2) 48 to 75 weight percent divinylbenzene, and 3) 0 to 20 weight percent of the optional styrene-type monomer. The amounts are based on the total weight of monomers in the monomer mixture. The amounts of each monomer in the monomer mixture are selected to provide a porous polymeric material (porous polymeric sorbent). That is, the amounts of each monomer are selected to provide a polymeric sorbent having a BET specific surface area that is at least 300 m$^2$/gram.

The amount of maleic anhydride used to form the porous polymeric sorbent may enhance the solubility of the carbon dioxide in the porous polymeric sorbent and may influence the total amount of carbon dioxide that can be sorbed. If the amount of maleic anhydride is lower than 8 weight percent based on the total weight of monomers in the monomer mixture, the solubility of carbon dioxide in the resulting porous polymeric sorbent may be unacceptably low. On the other hand, if the amount of maleic anhydride is greater than 52 weight percent (or even greater than 50 weight percent or greater than 45 weight percent or greater than 40 weight percent in some instances) based on the total weight of monomers in the monomer mixture, the resulting polymeric sorbent may not have a sufficiently high BET specific surface area. If the BET specific surface area is too low, the amount of carbon dioxide sorbed by the polymeric sorbent may be unacceptably low.

In some embodiments, the amount of maleic anhydride is at least 8 weight percent, at least 10 weight percent, at least 12 weight percent, at least 15 weight percent, or at least 20 weight percent. The amount of maleic anhydride can be up to 52 weight percent, up to 50 weight percent, up to 45 weight percent, up to 40 weight percent, up to 38 weight percent, up to 35 weight percent, up to 30 weight percent, or up to 25 weight percent. For example, the maleic anhydride may be present in a range of 8 to 52 weight percent, 8 to 50 weight percent, 8 to 45 weight percent, 8 to 40 weight percent, 8 to 38 weight percent, 10 to 40 weight percent, 10 to 35 weight percent, 10 to 30 weight percent, 10 to 25 weight percent, 15 to 40 weight percent, 15 to 35 weight percent, 15 to 30 weight percent, 15 to 25 weight percent, 20 to 40 weight percent, 20 to 35 weight percent, or 20 to 30 weight percent. The amounts are based on the total weight of monomers in the monomer mixture.

The amount of divinylbenzene crosslinker can have a strong influence on the BET specific surface area of the polymeric sorbent. The divinylbenzene contributes to the high crosslink density and to the formation of a rigid polymeric material having micropores and/or mesopores. The BET specific surface area tends to increase with an increase in the amount of divinylbenzene in the monomer mixture. If the amount of divinylbenzene in the monomer mixture is less than 48 weight percent, the polymeric material may not have a sufficiently high BET specific surface area. On the other hand, if the amount of divinylbenzene is greater than about 85 weight percent (or even greater than about 80 weight percent or greater than about 75 weight percent in some instances), the solubility of carbon dioxide in the polymeric sorbent may be undesirably low because there is not sufficient maleic anhydride in the monomer mixture.

In some embodiments, the amount of divinylbenzene is at least 48 weight percent, at least 50 weight percent, at least 55 weight percent, or at least 60 weight percent. The amount of divinylbenzene can be up to 85 weight percent, up to 80 weight percent, up to 75 weight percent, up to 70 weight percent, or up to 65 weight percent. For example, the divinylbenzene can be in a range of 48 to 85 weight percent, 48 to 80 weight percent, 48 to 75 weight percent, 50 to 75 weight percent, 50 to 70 weight percent, 50 to 65 weight percent, 55 to 75 weight percent, 55 to 70 weight percent, 55 to 65 weight percent, 60 to 75 weight percent, or 60 to 70 weight percent. The amounts are based on the total weight of monomers in the monomer mixture. In some specific embodiments, the amount of divinylbenzene is in a range of 50 to 65 weight percent based on the total weight of monomers in the monomer mixture.

Divinylbenzene can be difficult to obtain in a pure form. For example, divinylbenzene is often commercially available with purity as low as 55 weight percent. Obtaining divinylbenzene with purity greater man about 80 weight percent can be difficult and/or expensive. The impurities accompanying divinylbenzene are typically styrene-type monomers such as styrene, alkyl substituted styrene (e.g., ethyl styrene), or mixtures thereof. Thus, styrene-type monomers are often present in the monomer mixture along with divinylbenzene and maleic anhydride. The monomer mixture typically contains 0 to 20 weight percent styrene-type monomers based on a total weight of monomers in the monomer mixture. If the content of the styrene-type monomer is greater than 20 weight percent, the crosslink density may be too low and/or the distance between crosslinks may be too low to provide a polymeric sorbent with the desired high BET specific surface area (e.g., at least 300 $m^2$/gram). As the crosslink density decreases, the resulting polymeric sorbent tends to be less rigid and less porous.

Typically, divinylbenzene having a purity of 55 weight percent is not suitable for use in the monomer mixtures because the content of styrene-type monomer impurities is too high. That is, to provide a monomer mixture having a minimum amount of 48 weight percent divinylbenzene, the divinylbenzene often is at least about 80 weight percent pure. Using divinylbenzene having a lower purity than about 80 weight percent can result in the formation of a polymeric material with an undesirably low BET specific surface area.

In some embodiments, the amount of optional styrene-type monomers is at least 1 weight percent, at least 2 weight percent, or at least 5 weight percent. The amount of styrene-type monomer can be up to 20 weight percent, up to 15 weight percent, up to 12 weight percent, or up to 10 weight percent. For example, the amount of styrene-type monomer in the monomer mixture can be in a range of 0 to 20 weight percent, 1 to 20 weight percent, 2 to 20 weight percent, 5 to 20 weight percent, 5 to 15 weight percent, or 10 to 15 weight percent. The amounts are based on the total weight of monomers in the monomer mixture.

Overall, the monomer mixture typically includes 8 to 52 weight percent maleic anhydride based on a total weight of monomers in the monomer mixture, 48 to 85 weight percent divinylbenzene based on the total weight of monomers in the monomer mixture, and 0 to 20 weight percent styrene-type monomer based on the total weight of monomers in the monomer mixture. In other embodiments, the monomer mixture includes 8 to 40 weight percent maleic anhydride based on a total weight of monomers in the monomer mixture, 48 to 75 weight percent divinylbenzene based on the total weight of monomers in the monomer mixture, and 0 to 20 weight percent styrene-type monomer based on the total weight of monomers in the monomer mixture. In still other embodiments, the monomer mixture contains 10 to 40 weight percent maleic anhydride, 50 to 75 weight percent divinylbenzene, and 1 to 20 weight percent styrene-type monomer. In yet other embodiments, the monomer mixture contains 15 to 35 weight percent maleic anhydride, 55 to 75 weight percent divinylbenzene, and 1 to 20 weight percent styrene-type monomer. In still further embodiments, the monomer mixture contains 20 to 35 weight percent maleic anhydride, 55 to 75 weight percent divinylbenzene, and 1 to 20 weight percent styrene-type monomer. In yet further embodiments, the monomer mixture contains 20 to 35 weight percent maleic anhydride, 55 to 70 weight percent divinylbenzene, and 1 to 20 weight percent styrene-type monomers. In yet further embodiments, the monomer mixture contains 20 to 40 weight percent maleic anhydride, 50 to 70 weight percent divinylbenzene, and 5 to 20 weight percent styrene-type monomers.

Stated differently, polymeric sorbent includes 8 to 52 weight percent monomeric units of Formula (I), 48 to 85 weight percent monomeric units of Formula (II), and 0 to 20 weight percent monomeric units of Formula (III). In other embodiments, the polymeric sorbent includes 8 to 40 weight percent monomeric units of Formula (I), 48 to 75 weight percent monomeric units of Formula (II), and 0 to 20 weight percent monomeric units of Formula (III). In still other embodiments, the polymeric sorbent contains 10 to 40 weight percent monomeric units of Formula (I), 50 to 75 weight percent monomeric units of Formula (II), and 1 to 20 weight percent monomeric units of Formula (III). In yet other embodiments, the polymeric sorbent contains 15 to 35 weight percent monomeric units of Formula (I), 55 to 75 weight percent monomeric units of Formula (II), and 1 to 20 weight percent monomeric units of Formula (III). In still further embodiments, the polymeric sorbent contains 20 to 35 weight percent monomeric units of Formula (I), 55 to 75 weight percent monomeric units of Formula (II), and 1 to 20 weight percent monomeric units of Formula (III). In yet further embodiments, the polymeric sorbent contains 20 to 35 weight percent monomeric units of Formula (I), 55 to 70 weight percent monomeric units of Formula (II), and 1 to 20 weight percent monomeric units of Formula (III). In yet further embodiments, the polymeric sorbent contains 20 to 40 weight percent monomeric units of Formula (I), 50 to 70 weight percent monomeric units of Formula (II), and 5 to 20 weight percent monomeric units of Formula (III). The weight percent values are based on a total weight of the polymeric sorbent.

The monomer mixture typically contains at least 95 weight percent monomers selected from maleic anhydride, divinylbenzene, and styrene-type monomer. For example, at least 97 weight percent, at least 98 weight percent, at least 99 weight percent, at least 99.5 weight percent, at least 99.9 weight percent, or 100 weight percent of the monomers in the monomer mixture are selected from maleic anhydride, divinylbenzene, and styrene-type monomer. In many embodiments, the only monomers purposefully added to the monomer mixture are maleic anhydride and divinylbenzene with any other monomers being present (including the styrene-type monomers) as impurities in the maleic anhydride and the divinylbenzene. In some embodiments, where high purity divinylbenzene is used, the monomer mixture contains only divinylbenzene and maleic anhydride. That is, the sum of the amount of divinylbenzene and maleic anhydride is 100 weight percent.

Stated differently, at least 95 weight percent of the monomeric units included in the polymeric sorbent are selected from Formula (I), Formula (II), and Formula (III). For example, at least 97 weight percent, at least 98 weight percent, at least 99 weight percent, at least 99.5 weight percent, at least 99.9 weight percent, or 100 weight percent of the monomeric units in the polymeric sorbent are of Formula (I), Formula (II), and Formula (III). In some embodiments, where high purity divinylbenzene is used to form the polymeric sorbent, the only monomeric units are of Formula (I) and Formula (II). That is, the sum of the monomeric units of Formula (I) and Formula (II) is 100 weight percent.

In addition to the monomer mixture, the polymerizable composition used to form the porous polymeric sorbent includes an organic solvent. The polymerizable composition is a single phase prior to polymerization. Stated differently, prior to polymerization, the polymerizable composition is not a suspension. The organic solvent is selected to dissolve the monomers included in the monomer mixture and to solubilize the polymeric material (polymeric sorbent) as it begins to form. The organic solvent includes a ketone, ester, acetonitrile, or mixture thereof.

The organic solvent can function as a porogen during formation of the porous polymeric sorbent. The organic solvent choice can strongly influence the BET specific surface area and the size of the pores formed in the polymeric sorbent. Using organic solvents that are miscible with both the monomers and the forming polymer tend to result in the formation of polymeric material having micropores and mesopores. Good solvents for the monomers and the forming polymer tend to result in a larger fraction of the porosity of the final polymeric sorbent being in the form of micropores and mesopores.

Organic solvents that are particularly suitable include ketones, esters, acetonitrile, and mixtures thereof. Other organic solvents can be added along with one or more of these organic solvents provided that the resulting polymeric sorbent has a BET specific surface area equal to at least 300 $m^2$/gram. Examples of suitable ketones include, but are not limited to, alkyl ketones such as methyl ethyl ketone and methyl isobutyl ketone. Examples of suitable esters include, but are not limited to, acetate esters such as ethyl acetate, propyl acetate, butyl acetate, amyl acetate, and tert-butyl acetate.

The organic solvent can be used in any desired amount. The polymerizable compositions often have percent solids in a range of 1 to 75 weight percent (e.g., the polymerizable composition contains 25 to 99 weight percent organic solvent). If the percent solids are too low, the polymerization time may become undesirably long. The percent solids are often at least 1 weight percent, at least 2 weight percent, at least 5 weight percent, at least 10 weight percent, or at least 15 weight percent. If the percent solids are too great, however, the viscosity may be too high for effective mixing. Further, increasing the percent solids tends to result in the formation of polymeric sorbent with a lower BET specific surface area. The percent solids can be up to 75 weight percent, up to 70 weight percent, up to 60 weight percent, up to 50 weight percent, up to 40 weight percent, up to 30 weight percent, or up to 25 weight percent. For example, the percent solids can be in a range of 5 to 75 weight percent, 5 to 50 weight percent, 5 to 40 weight percent, 5 to 30 weight percent, or 5 to 25 weight percent.

In addition to the monomer mixture and organic solvent, the polymerizable compositions typically include an initiator for free radical polymerization reactions. Any suitable free radical initiator can be used. Suitable free radical initiators are typically selected to be miscible with the monomers included in the polymerizable composition. In some embodiments, the free radical initiator is a thermal initiator that can be activated at a temperature above room temperature. In other embodiments, the free radical initiator is a redox initiator. Because the polymerization reaction is a free radical reaction, it is desirable to minimize the amount of oxygen in the polymerizable composition.

Both the type and amount of initiator can affect the polymerization rate. In general, increasing the amount of the initiator tends to lower the BET specific surface area; however, if the amount of initiator is too low, it may be difficult to obtain high conversions of the monomers to polymeric material. The free radical initiator is typically present in an amount in a range of 0.05 to 10 weight percent, 0.05 to 8 weight percent, 0.05 to 5 weight percent, 0.1 to 10 weight percent, 0.1 to 8 weight percent, 0.1 to 5 weight percent, 0.5 to 10 weight percent, 0.5 to 8 weight percent, 0.5 to 5 weight percent, 1 to 10 weight percent, 1 to 8 weight percent, or 1 to 5 weight percent. The weight percent is based on a total weight of monomers in the polymerizable composition.

Suitable thermal initiators include organic peroxides and azo compounds. Example azo compounds include, but are not limited to, those commercially available under the trade designation VAZO from E.I. du Pont de Nemours & Co. (Wilmington, Del.) such as VAZO 64 (2,2'-azobis(isobutyronitrile), which is often referred to as AIBN), and VAZO 52 (2,2'-azobis(2,4-dimethylpentanenitrile)). Other azo compounds are commercially available from Wako Chemicals USA, Inc. (Richmond, Va.) such as V-601 (dimethyl 2,2'-azobis(2-methylproprionate)), V-65 (2,2'-azobis(2,4-dimethyl valeronitrile)), and V-59 (2,2'-azobis(2-methylbutyronitrile)). Organic peroxides include, but are not limited to, bis(1-oxoaryl)peroxides such as benzoyl peroxide (BPO), bis(1-oxoalkyl)peroxides such as lauroyl peroxide, and dialkyl peroxides such as dicumyl peroxide or di-tert-butyl peroxide and mixtures thereof. The temperature needed to activate the thermal initiator is often in a range of 25° C. to 160° C., in a range of 30° C. to 150° C., in a range of 40°

C. to 150° C., in a range of 50° C. to 150° C., in a range of 50° C. to 120° C., or in a range of 50° C. to 110° C.

Suitable redox initiators include arylsulfinate salts, triarylsulfonium salts, or N,N-dialkylaniline (e.g., N,N-dimethylaniline) in combination with a metal in an oxidized state, a peroxide, or a persulfate. Specific arylsulfinate salts include tetraalkylammonium arylsulfinates such as tetrabutylammonium 4-ethoxycarbonylbenzenesulfinate, tetrabutylammonium 4-trifluoromethylbenzenesulfinate, and tetrabutylammonium 3-trifluoromethylbenzenesulfinate. Specific triarylsulfonium salts include those with a triphenylsulfonium cation and with an anion selected from $PF_6^-$, $AsF_6^-$, and $SbF_6^-$. Suitable metal ions include, for example, ions of group III metals, transition metals, and lanthanide metals. Specific metal ions include, but are not limited to, Fe(III), Co(III), Ag(I), Ag(II), Cu(II), Ce(III), Al (III), Mo(VI), and Zn(II). Suitable peroxides include benzoyl peroxide, lauroyl peroxide, and the like. Suitable persulfates include, for example, ammonium persulfate, tetraalkylammonium persulfate (e.g., tetrabutylammonium persulfate), and the like.

The polymerizable composition is typically free or substantially free of surfactants. As used herein, the term "substantially free" in reference to the surfactant means that no surfactant is purposefully added to the polymerizable composition and any surfactant that may be present is the result of being an impurity in one of the components of the polymerizable composition (e.g., an impurity in the organic solvent or in one of the monomers). The polymerizable composition typically contains less than 0.5 weight percent, less than 0.3 weight percent, less than 0.2 weight percent, less than 0.1 weight percent, less than 0.05 weight percent, or less than 0.01 weight percent surfactant based on the total weight of the polymerizable composition. The absence of a surfactant is advantageous because these materials tend to restrict access to and, in some cases, fill micropores and mesopores in a porous material.

When the polymerizable composition is heated in the presence of a free radical initiator, polymerization of the monomers in the monomer mixture occurs. By balancing the amounts of each monomer in the monomer mixture and by selecting an organic solvent that can solubilize all of the monomers and the growing polymeric material during its early formation stage, a polymeric sorbent can be prepared that has a BET specific surface area equal to at least 300 $m^2$/gram. The BET specific surface area of the polymeric sorbent can be at least 350 $m^2$/gram, at least 400 $m^2$/gram, at least 450 $m^2$/gram, or at least 500 $m^2$/gram. The BET specific surface area can be, for example, up to 1000 $m^2$/gram or higher, up to 900 $m^2$/gram, up to 800 $m^2$/gram, up to 750 $m^2$/gram, or up to 700 $m^2$/gram.

Figure 2:
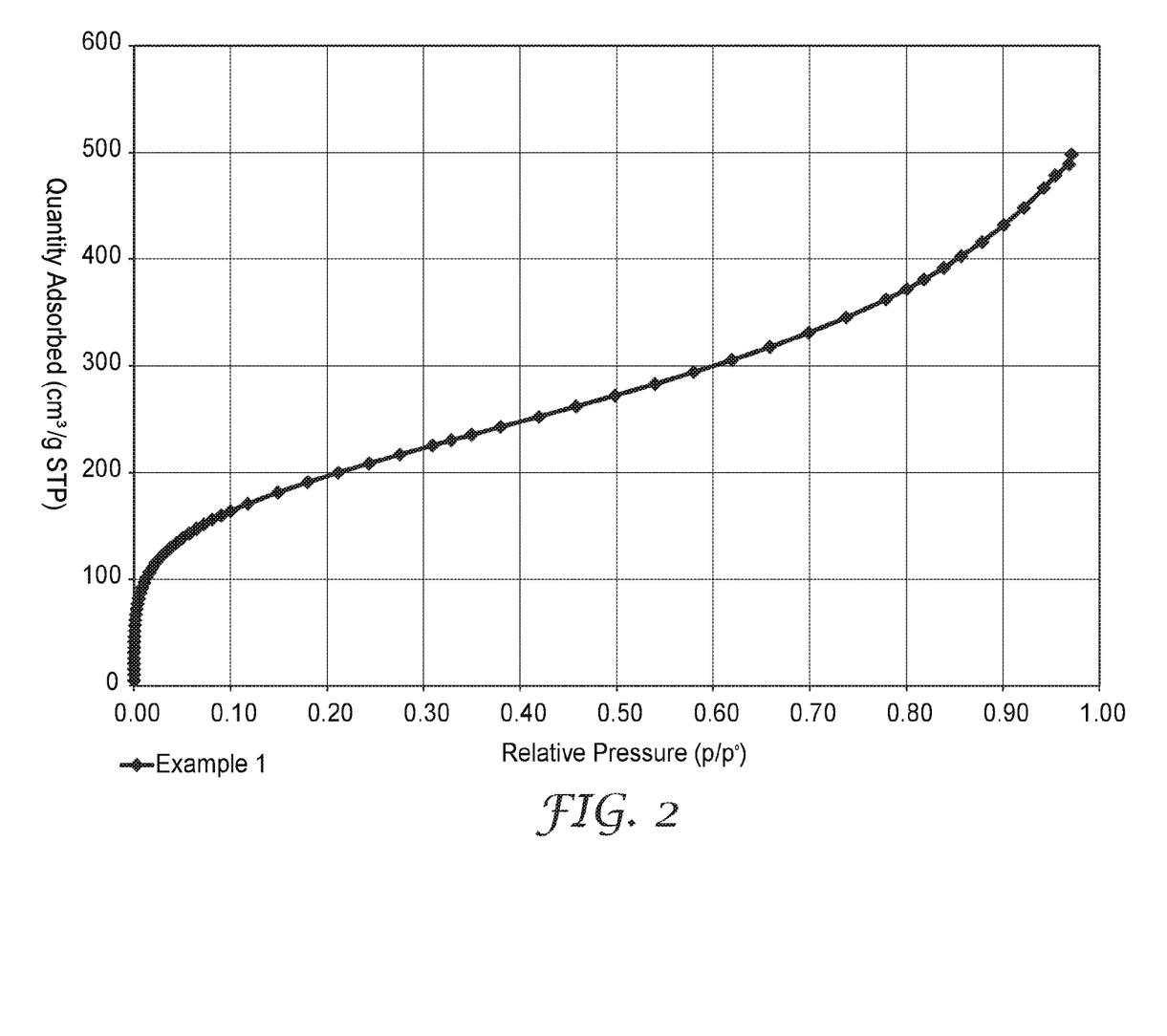
FIG. 2 is the argon adsorption isotherm at 77° K and at relative pressures up to 0.98±0.01 for an exemplary porous polymeric sorbent.

The high BET specific surface area is at least partially attributable to the presence of micropores and/or mesopores in polymeric sorbent. The argon adsorption isotherms (at 77° K) of the polymeric sorbent indicate that there is considerable adsorption of argon at relative pressures below 0.1, which suggests that micropores are present. There is a gradual increase in adsorption at relative pressures between 0.1 and about 0.95. This increase is indicative of a wide size distribution of mesopores. An argon adsorption isotherm is shown in FIG. 2 for an example porous polymeric sorbent.

In some embodiments, at least 20 percent of the BET specific surface area of the polymeric sorbent is attributable to the presence of micropores and/or mesopores. The percentage of the BET specific surface area attributable to the presence of micropores and/or mesopores can be at least 25 percent, at least 30 percent, at least 40 percent, at least 50 percent, or at least 60 percent. In some embodiments, the percentage of the BET specific surface area attributable to the presence of micropores and/or mesopores can be up to 90 percent or higher, up to 80 percent or higher, or up to 75 percent or higher.

The porous polymeric sorbent has a total pore volume equal to at least 0.25 $cm^3$/gram. Total pore volume is calculated from the amount of argon adsorbed at liquid nitrogen temperature (77° K) at a relative pressure)($p/p°$ equal to approximately 0.98 (i.e., 0.98±0.01). In some embodiments, the total pore volume is at least 0.30 $cm^3$/grams, at least 0.40 $cm^3$/gram, at least 0.50 $cm^3$/gram, or at least 0.60 $cm^3$/gram. The total pore volume can be up to 1.2 $cm^3$/gram or even higher, up to 1.0 $cm^3$/gram, or up to 0.8 $cm^3$/gram.

The structure of the divinylbenzene/maleic anhydride polymeric material is particularly well suited to form a porous polymeric sorbent. Providing that the content of monomeric units of Formula (III) are low, the divinylbenzene/maleic anhydride polymeric material has alternating units of Formula (I) and Formula (II). This structure results in high crosslinking and contributes to the formation of a porous polymeric material, particularly a porous polymeric material having a high content of micropores and/or mesopores. The replacement of maleic anhydride with an ethylenically unsaturated monomer may not result in the formation of a polymeric material that has such high BET specific surface area and a large pore volume.

The porous polymeric sorbent sorbs carbon dioxide. Thus, in another aspect, a composition is provided that includes the porous polymeric sorbent and carbon dioxide sorbed on the porous polymeric sorbent. The porous polymeric sorbent is the same as described above. The amount of carbon dioxide that sorbs on the porous polymeric sorbent tends to increase with pressure. For example, the amount of carbon dioxide sorbed in mmoles/gram at room temperature (e.g., 25° C.) and 20 bar is often at least 3 times greater than the amount sorbed in mmoles/gram at room temperature (e.g., 25° C.) and 1 bar. That is, the ratio of the amount sorbed in mmoles/gram at room temperature (e.g., 25° C.) and 20 bar to the amount sorbed in mmoles/gram at room temperature (e.g., 25° C.) and 1 bar is at least 3. For example, this ratio can be at least 4, at least 5, or at least 6 and can be up to 10 or more, up to 9, up to 8, or up to 7.

Stated differently, the difference in the amount of carbon dioxide sorbed at room temperature (e.g., 25° C.) and 20 bar and the amount of carbon dioxide sorbed at room temperature (e.g., 25° C.) and 1 bar is often at least 2 mmoles/gram, at least 3 mmoles/gram, at least 4 mmoles/gram, or at least 5 mmoles/gram. The amount can be up to 10 mmoles/gram, up to 8 mmoles/gram, or up to 6 mmoles/gram.

The amount of carbon dioxide sorbed at room temperature (e.g., 25° C.) and 20 bar is often at least 2 mmoles/gram, at least 2.5 mmoles/gram, at least 3 mmoles/gram, at least 3.5 mmoles/gram, at least 4 mmoles/gram, at least 4.5 mmoles/gram, at least 5 mmoles/gram, at least 5.5 mmoles/gram, at least 6 mmoles/gram, at least 7 mmoles/gram, at least 8 mmoles/gram, or at least 10 mmoles/gram.

The amount of carbon dioxide sorbed at room temperature (e.g., 25° C.) and 20 bar is often at least 10 weight percent based on the weight of the polymeric sorbent. The amount sorbed can be at least 12 weight percent, at least 14 weight percent, at least 16 weight percent, at least 18 weight percent, at least 20 weight percent, at least 22 weight percent, at least 24 weight percent, at least 25 weight percent, at least 30 weight percent, at least 35 weight percent, at least 40 weight percent, or at least 45 weight percent.

Figure 1:
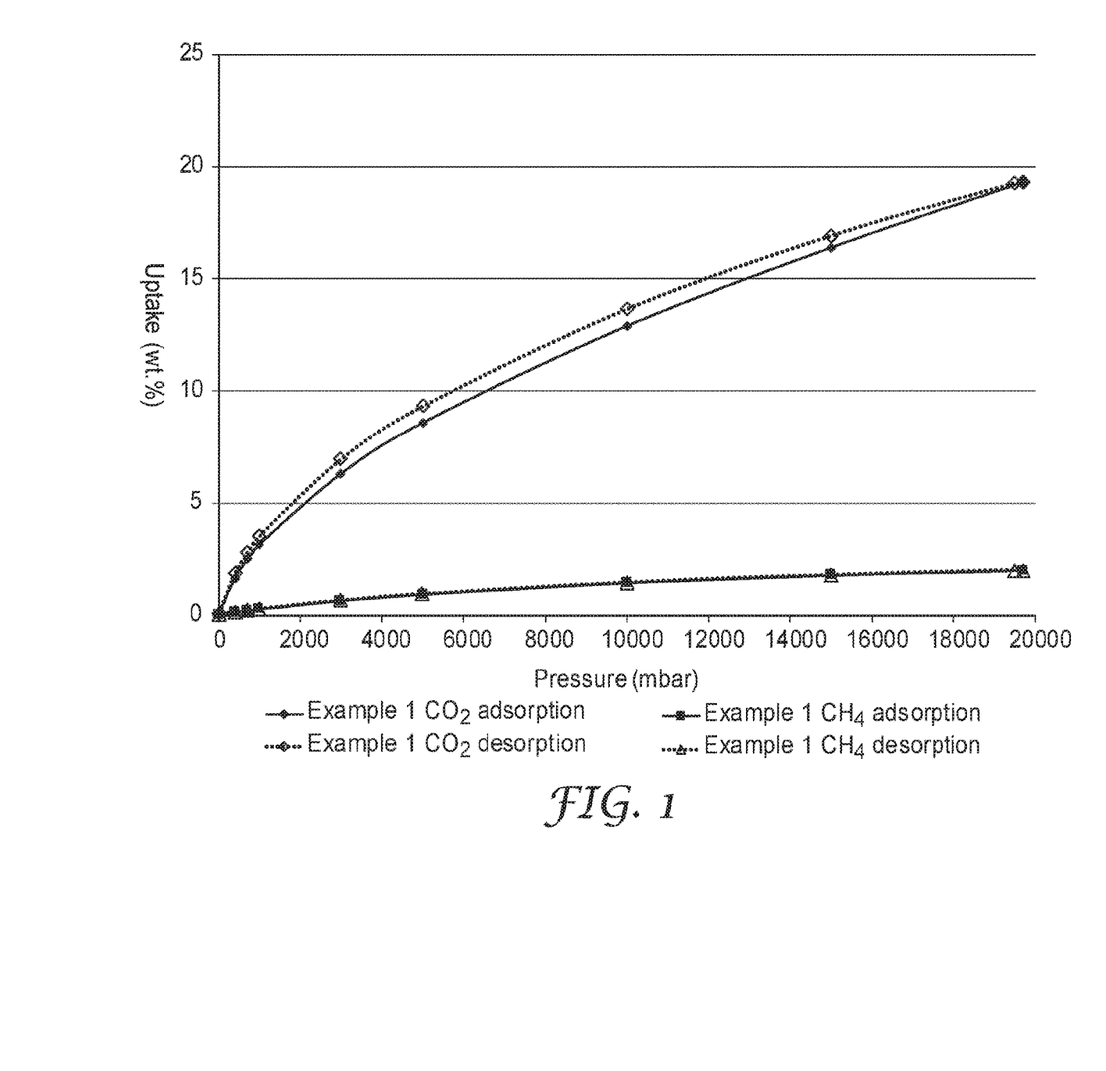
FIG. 1 is a plot of the adsorption and desorption isotherms at 25° C. and at pressures up to about 20 bar for both carbon dioxide and methane on an exemplary porous polymeric sorbent.

FIG. 1 is a plot showing the adsorption and desorption of both carbon dioxide and methane at pressures up to about 20 bar at 25° C. for an example porous polymeric sorbent. There is only a small amount of hysteresis between the adsorption and desorption curves. This may suggest that the pores of the polymeric sorbent can be both filled and emptied easily with either carbon dioxide or methane. The amount of carbon dioxide that is sorbed at a first pressure such as, for example, at 20 bar or even greater can be reduced substantially by simply decreasing the pressure to a second pressure that is lower than the first pressure. The second pressure is often greater than or equal to 1 bar or ambient pressure. No vacuum or heat is needed to substantially reduce the amount of carbon dioxide sorbed on the porous polymeric sorbent at room temperature (e.g., 25° C.). For example, the amount of carbon dioxide sorbed at room temperature (e.g., 25° C.) and 20 bar can be reduced by at least 60 weight percent, at least 70 weight percent, at least 80 weight percent, or at least 90 weight percent by lowering the pressure to about 1 bar. The porous polymeric sorbent can be used repeatedly to sorb and to desorb carbon dioxide by cycling the pressure from a first pressure such as, for example, about 20 bar to a second pressure such as, for example, about 1 bar.

The polymeric sorbent selectively sorbs carbon dioxide over methane. For example, the amount of sorbed carbon dioxide at room temperature (e.g., 25° C.) and 20 bar is often at least 2 times greater than the amount of sorbed methane at room temperature (e.g., 25° C.) and 20 bar. That is, the ratio of the amount of carbon dioxide (in mmoles/gram) to the amount of methane (in mmoles/gram) sorbed at room temperature (e.g., 25° C.) and 20 bar is at least 2. For example, this ratio can be at least 2.5, at least 3, at least 3.5, at least 4, at least 4.5, or at least 5 and can be up to 10, up to 8, or up to 6. Selectivity for the sorption of carbon dioxide over hydrogen is expected to be at least as good as the selectivity for the sorption of carbon dioxide over methane.

Some polymeric materials that have been used for sorption of carbon dioxide have acidic groups. Compared to these known polymeric materials, the porous polymeric sorbents based on maleic anhydride and divinylbenzene are more hydrophobic. These more hydrophobic porous polymeric sorbents may be preferable when water vapor is present in the gas mixtures. Water is not likely to be sorbed in significant amounts and is not likely to adversely interfere with the capture efficiency of carbon dioxide on the porous polymeric sorbent.

Other polymeric materials that have been used for sorption of carbon dioxide have no functional groups. More specifically, these previously used polymeric materials are aromatic hydrocarbon-based sorbents. While such polymeric materials are likely to have low water sorption, they may not be as effective as the porous polymeric sorbents described herein that have anhydride groups. Although not wishing to be bound by theory, the anhydride groups may facilitate solubility of the carbon dioxide within the porous polymeric sorbents. That is, sorption may occur by a combination of pore filling and swelling of the porous polymeric sorbent.

Various embodiments are provided that are methods of sorbing carbon dioxide on a porous polymeric sorbent and a composition resulting from the sorption of carbon dioxide on the porous polymeric sorbent. The porous polymeric sorbent is a divinylbenzene/maleic anhydride polymeric material that has micropores and/or mesopores.

Embodiment 1A is a method of sorbing carbon dioxide on a porous polymeric sorbent. The method includes providing a polymeric sorbent having a BET specific surface area equal to at least 300 m$^2$/gram. The porous polymeric sorbent comprises (a) 8 to 52 weight percent of a first monomeric unit of Formula (I), (b) 48 to 85 weight percent of a second monomeric unit of Formula (II), and (c) 0 to 20 weight percent of a third monomeric unit of Formula (III) wherein R$^1$ is hydrogen or alkyl.

Each weight percent is based on a total weight of the porous polymeric sorbent. Each asterisk (*) denotes the location of attachment of the monomeric unit to another monomeric unit or to a terminal group. The method further includes exposing the porous polymeric sorbent to a gas mixture containing carbon dioxide and sorbing carbon dioxide on the porous polymeric sorbent.

Embodiment 2A is the method of embodiment 1A, wherein the porous polymeric sorbent comprises (a) 8 to 40 weight percent of the first monomeric unit of Formula (I), (b) 48 to 75 weight percent of the second monomeric unit of Formula (II), and (c) 0 to 20 weight percent of the third monomeric unit of Formula (III).

Embodiment 3A is the method of embodiment 1A or 2A, wherein the porous polymeric sorbent comprises (a) 10 to 40 weight percent of the first monomeric unit of Formula (I), (b) 50 to 75 weight percent of the second monomeric unit of Formula (II), and (c) 1 to 20 weight percent of the third monomeric unit of Formula (III).

Embodiment 4A is the method of any one of embodiments 1A to 3A, wherein the porous polymeric sorbent comprises (a) 15 to 35 weight percent of the first monomeric unit of Formula (I), (b) 55 to 75 weight percent of the second monomeric unit of Formula (II), and (c) 1 to 20 weight percent of the third monomeric unit of Formula (III).

Embodiment 5A is the method of any one of embodiments 1A to 4A, wherein the porous polymeric sorbent comprises (a) 20 to 35 weight percent of the first monomeric unit of Formula (I), (b) 55 to 75 weight percent of the second monomeric unit of Formula (II), and (c) 0 to 20 weight percent of the third monomeric unit of Formula (III).

Embodiment 6A is the method of any of embodiments 1A to 5A, wherein the porous polymeric sorbent comprises (a) 20 to 40 weight percent of the first monomeric unit of Formula (I), (b) 50 to 70 weight percent of the second monomeric unit of Formula (II), and (c) 5 to 20 weight percent of the third monomeric unit of Formula (III).

Embodiment 7A is the method of any one of embodiments 1A to 6A, wherein the porous polymeric sorbent has a total pore volume of at least 0.25 cm$^3$/gram, the total pore volume being measured by adsorbing argon at 77° K at a relative pressure equal to 0.98±0.01.

Embodiment 8A is the method of any one of embodiments 1A to 7A, wherein the total pore volume is at least 0.30 cm$^3$/gram.

Embodiment 9A is the method of any one of embodiments 1A to 8A, wherein the total pore volume is at least 0.40 cm$^3$/gram or at least 0.80 cm$^3$/gram.

Embodiment 10A is the method of any one of embodiments 1A to 9A, wherein the BET specific surface area of the porous polymeric sorbent is at least 400 m$^2$/gram or at least 500 m$^2$/gram.

Embodiment 11A is the method of any one of embodiments 1A to 10A, wherein at least 50 percent of the BET specific surface area is attributable to micropores, mesopores, or a combination thereof.

Embodiment 12A is the method of any one of embodiments 1A to 11A, wherein an amount of carbon dioxide sorbed on the porous polymeric sorbent is at least 2 mmoles/gram (i.e., 2 mmoles carbon dioxide per gram of porous polymeric sorbent) at room temperature (e.g., 25° C.) and 20 bar.

Embodiment 13A is the method of any one of embodiments 1A to 12A, wherein an amount of carbon dioxide sorbed on the porous polymeric sorbent is at least 3 mmoles/gram at room temperature (e.g., 25° C.) and 20 bar.

Embodiment 14A is the method of any one of embodiments 1A to 13A, wherein an amount of carbon dioxide sorbed on the porous polymeric sorbent is at least 4 mmoles/gram (i.e., 4 mmoles carbon dioxide per gram of porous polymeric sorbent) at room temperature (e.g., 25° C.) and 20 bar.

Embodiment 15A is the method of any one of embodiments 1A to 14A, wherein an amount of carbon dioxide sorbed on the porous polymeric sorbent in mmoles/gram is at least 3 times greater at room temperature (e.g., 25° C.) and 20 bar than at room temperature (e.g., 25° C.) and 1 bar.

Embodiment 16A is the method of any one of embodiments 1A to 15A, wherein sorbing occurs at a first pressure and the method further comprises removing carbon dioxide sorbed on the porous polymeric sorbent at a second pressure that is lower than the first pressure and that is greater than or equal to ambient pressure or 1 bar.

Embodiment 17A is the method of any one of embodiments 1A to 16A, wherein the gas mixture comprises carbon dioxide and methane and wherein an amount of carbon dioxide sorbed on the porous polymeric sorbent in grams/mole at room temperature (e.g., 25° C.) and 20 bar is at least 2 times greater than an amount of methane sorbed on the porous polymeric sorbent in grams/mole at room temperature (e.g., 25° C.) and 20 bar.

Embodiment 1B is a composition that includes (a) a porous polymeric sorbent and (b) carbon dioxide sorbed on the porous polymeric sorbent. The porous polymeric sorbent comprises (i) 8 to 52 weight percent of a first monomeric unit of Formula (I), (ii) 48 to 85 weight percent of a second monomeric unit of Formula (II), and (iii) 0 to 20 weight percent of a third monomeric unit of Formula (III) wherein R$^1$ is hydrogen or alkyl.

Each weight percent is based on a total weight of the porous polymeric sorbent. Each asterisk (*) denotes the location of attachment of the monomeric unit to another monomeric unit or to a terminal group.

Embodiment 2B is the composition of embodiment 1B, wherein the porous polymeric sorbent comprises (a) 8 to 40 weight percent of the first monomeric unit of Formula (I), (b) 48 to 75 weight percent of the second monomeric unit of Formula (II), and (c) 0 to 20 weight percent of the third monomeric unit of Formula (III).

Embodiment 3B is the composition of embodiment 1B or 2B, wherein the porous polymeric sorbent comprises (a) 10 to 40 weight percent of the first monomeric unit of Formula (I), (b) 50 to 75 weight percent of the second monomeric unit of Formula (II), and (c) 1 to 20 weight percent of the third monomeric unit of Formula (III).

Embodiment 4B is the composition of any one of embodiments 1B to 3B, wherein the porous polymeric sorbent comprises (a) 15 to 35 weight percent of the first monomeric unit of Formula (I), (b) 55 to 75 weight percent of the second monomeric unit of Formula (II), and (c) 1 to 20 weight percent of the third monomeric unit of Formula (III).

Embodiment 5B is the composition of any one of embodiments 1B to 4B, wherein the porous polymeric sorbent comprises (a) 20 to 35 weight percent of the first monomeric unit of Formula (I), (b) 55 to 75 weight percent of the second monomeric unit of Formula (II), and (c) 0 to 20 weight percent of the third monomeric unit of Formula (III).

Embodiment 6B is the composition of any one of embodiments 1B to 5B, wherein the porous polymeric sorbent comprises (a) 20 to 40 weight percent of the first monomeric unit of Formula (I), (b) 50 to 70 weight percent of the second monomeric unit of Formula (II), and 5 to 20 weight percent of the third monomeric unit of Formula (III).

Embodiment 7B is the composition of any one of embodiments 1B to 6B, wherein the porous polymeric sorbent has a total pore volume of at least 0.25 cm$^3$/gram, the total pore volume being measured by adsorbing argon at 77° K at a relative pressure equal to 0.98±0.01.

Embodiment 8B is the composition of any one of embodiments 1B to 7B, wherein the total pore volume is at least 0.30 cm$^3$/gram.

Embodiment 9B is the composition of any one of embodiments 1B to 8B, wherein the total pore volume is at least 0.40 cm$^3$/gram or at least 0.80 cm$^3$/gram.

Embodiment 10B is the composition of any one of embodiments 1B to 9B, wherein the BET specific surface area of the porous polymeric sorbent is at least 400 m$^2$/gram or at least 500 m$^2$/gram.

Embodiment 11B is the composition of any one of embodiments 1B to 10B, wherein at least 50 percent of the BET specific surface area is attributable to micropores, mesopores, or a combination thereof.

Embodiment 12B is the composition of any one of embodiments 1B to 11B, wherein an amount of carbon dioxide sorbed on the porous polymeric sorbent is at least 2 mmoles/gram (i.e., 2 mmoles carbon dioxide per gram of porous polymeric sorbent) at room temperature (e.g., 25° C.) and 20 bar.

Embodiment 13B is the composition of any one of embodiments 1B to 12B, wherein an amount of carbon dioxide sorbed on the porous polymeric sorbent is at least 3 mmoles/gram at room temperature (e.g., 25° C.) and 20 bar.

Embodiment 14B is the composition of any one of embodiments 1B to 13B, wherein an amount of carbon dioxide sorbed on the porous polymeric sorbent is at least 4 mmoles/gram at room temperature (e.g., 25° C.) and 20 bar.

Embodiment 15B is the composition of any one of embodiments 1B to 14B, wherein an amount of carbon dioxide sorbed on the porous polymeric sorbent in mmoles/gram is at least 3 times greater at room temperature (e.g., 25° C.) and 20 bar than at room temperature (e.g., 25° C.) and 1 bar.

EXAMPLES

TABLE 1

List of materials

| Chemical Name | Chemical Supplier |
| --- | --- |
| Divinylbenzene (DVB) (80% tech grade), which contained 80 weight percent DVB and 20 weight percent styrene-type monomers. The calculation of moles of DVB used to prepare the polymeric material does take into account the purity. | Sigma-Aldrich, Milwaukee, WI |
| Maleic anhydride (MA) | Alfa Aesar, Ward Hill, MA |
| Benzoyl peroxide (BPO) | Sigma-Aldrich, Milwaukee, WI |
| Ethyl acetate (EtOAc) | EMD Millipore Chemicals, Billerica, MA |

Argon Adsorption Analysis:

Porosity and gas sorption experiments were performed using a Micromeritics Instrument Corporation (Norcross, Ga.) accelerated surface area and porosimetry (ASAP) 2020 system using adsorbates of ultra-high purity. The following is a typical method used for the characterization of the porosity within the exemplified porous polymeric sorbents. In a Micromeritics half inch diameter sample tube, 50 to 250 milligrams of material was degassed by heating for two hours at 150° C. under ultra-high vacuum (3 to 7 micrometers Hg) on the analysis port of the ASAP 2020 to remove residual solvent and other adsorbates. Argon sorption isotherms at 77° K were obtained using low pressure dosing (5 cm$^3$/g) at a relative pressure)(p/p°) less than 0.1 and a pressure table of linearly spaced relative pressure points in a range from 0.1 to 0.98. The method for all isotherms made use of the following equilibrium intervals: 90 seconds at p/p° less than $10^{-5}$, 40 seconds at p/p° in a range of $10^{-5}$ to 0.1, and 20 seconds at p/p° greater than 0.1. Helium was used for the free space determination, after argon sorption analysis, both at ambient temperature and at 77° K. BET specific surface areas ($SA_{BET}$) were calculated from argon adsorption data by multipoint Brunauer-Emmett-Teller (BET) analysis. Apparent micropore distributions were calculated from argon adsorption data by density functional theory (DFT) analysis using the argon at 77° K on carbon slit pores by non-linear density functional theory (NLDFT) model. Total pore volume was calculated from the total amount of argon adsorbed at a relative pressure)(p/p° equal to approximately 0.98. BET, DFT and total pore volume analyses were performed using Micromeritics MicroActive Version 1.01 software.

Carbon Dioxide and Methane Adsorption Analysis:

A high pressure microgravimetric gas sorption system model IGA-001 from Hiden Analytical (Warrington, U.K.) was used to measure the $CO_2$ and $CH_4$ adsorption isotherms for the porous polymeric sorbent at 25° C. This automated instrument integrates precise computer-control and measurement of weight change, pressure, and temperature during measurements to determine the gas adsorption/desorption isotherms of small quantities of materials. The following is a general procedure for the $CO_2$ and $CH_4$ adsorption/desorption isotherm measurement of the porous polymeric sorbents exemplified.

Prior to measurements, approximately 100 mg of a porous polymeric sorbent was loaded onto the quartz crucible provided with the instrument. The crucible was then attached to the internal suspension rods of the microbalance. The sample was degassed at 150° C. for 8 hours under high vacuum (<1 mmHg). After degassing, the weight of the sample was recorded and set as the initial reference weight for adsorption. Ultrahigh purity gases ($CO_2$ or $CH_4$) were introduced in predetermined pressure steps, starting from vacuum and going up to 20 bar. During measurements, the sample temperature was kept constant (25.0±0.05° C.) by using a circulating water bath. After each variation of pressure, the weight relaxation was monitored in real time by the instrument's software, and the asymptotic equilibrium weight was calculated. After equilibration at each pressure level, a new pressure change was caused, and the system moved to the next isotherm point. A normal cycle consisted of an adsorption branch (vacuum to 20 bar) and a reversed desorption branch (20 bar down to vacuum). Buoyancy corrections were made by using the skeletal density of the porous polymeric sorbent obtained from helium pycnometry measurements. The precision of gravimetric measurements is estimated to be ±0.01 wt. % for a 100 mg sample at a pressure of 20 bar.

Example 1

In a 5 L round-bottom flask, 80.3 grams (493 mmoles) of DVB (80 wt. %, tech grade), 30.3 grams (309 mmoles) of MA, and 2.25 grams (9.29 mmoles) of BPO were dissolved in 2153 grams of EtOAc. The polymerizable composition had 5.0 wt. % solids in EtOAc and contained a monomer mixture (58.1 wt. % DVB, 27.3 wt. % MA, and 14.5 wt. % styrene-type monomers based on the total weight of monomers) plus 2 wt. % BPO (based on the total weight of monomers). The polymerizable composition was bubbled with nitrogen for 30 minutes. The flask was then capped and placed in a sand bath at 95° C. The polymerizable composition was heated at this elevated temperature for 18 hours. A white precipitate that had formed was isolated by vacuum filtration and washed with EtOAc. The solid was divided up and placed in three 32 ounce jars. The jars were then each filled with 750 mL of EtOAc. The solids were allowed to stand in EtOAc for one hour at room temperature. The solids were again isolated by vacuum filtration and washed with EtOAc. The solid was divided up again and placed in three 32 ounce jars. The jars were then each filled with 750 mL of EtOAc. The solids were allowed to stand in EtOAc overnight. The solids were again isolated by vacuum filtration and washed with EtOAc. The solid was then dried under high vacuum at 95° C. for eight hours.

This porous polymeric sorbent had a $SA_{BET}$ of 637.6 $m^2$/gram and a total pore volume of 0.637 $cm^3$/gram ($p/p°$ equal to 0.971) as determined by argon adsorption. The argon adsorption isotherm is shown in FIG. 2. This porous polymeric sorbent adsorbed 4.39 mmoles/gram (19.3 wt. % uptake) $CO_2$ at 20 bar and 0.70 mmoles/gram (3.1 wt. % uptake) $CO_2$ at 1 bar. This porous polymeric sorbent adsorbed 1.25 mmoles/gram (2.0 wt. % uptake) $CH_4$ at 20 bar and 0.16 mmoles/gram (0.26 wt. % uptake) $CH_4$ at 1 bar. FIG. 1 contains a plot for both carbon dioxide adsorption and desorption, as well as, methane adsorption and desorption at various pressures up to 20 bar for this porous polymeric sorbent.

We claim:

1. A method of sorbing carbon dioxide on a porous polymeric sorbent, the method comprising:
   providing the porous polymeric sorbent, wherein the porous polymeric sorbent has a BET specific surface area equal to at least 300 $m^2$/gram, the porous polymeric sorbent comprising
   (a) 8 to 52 weight percent of a first monomeric unit of Formula (I);

(I)

(b) 48 to 85 weight percent of a second monomeric unit of Formula (II); and (II)

(c) 0 to 20 weight percent of a third monomeric unit of Formula (III) wherein $R^1$ is hydrogen or alkyl; and (III)

exposing the porous polymeric sorbent to a gas mixture comprising carbon dioxide; and
   sorbing carbon dioxide on the porous polymeric sorbent.

2. The method of claim 1, wherein the porous polymeric sorbent comprises (a) 8 to 40 weight percent of the first monomeric unit of Formula (I), (b) 48 to 75 weight percent of the second monomeric unit of Formula (II), and (c) 0 to 20 weight percent of the third monomeric unit of Formula (III).

3. The method of claim 1, wherein the porous polymeric sorbent comprises (a) 20 to 40 weight percent of the first monomeric unit of Formula (I), (b) 50 to 70 weight percent of the second monomeric unit of Formula (II), and (c) 5 to 20 weight percent of the third monomeric unit of Formula (III).

4. The method of claim 1, wherein the porous polymeric sorbent has a total pore volume of at least 0.25 $cm^3$/gram, the total pore volume being measured by adsorbing argon at 77° K at a relative pressure equal to 0.98±0.01.

5. The method of claim 1, wherein the BET specific surface area of the porous polymeric sorbent is at least 400 $m^2$/gram.

6. The method of claim 1, wherein at least 50 percent of the BET specific surface area is attributable to micropores, mesopores, or a combination thereof.

7. The method of claim 1, wherein at least 2 mmoles of carbon dioxide are sorbed per gram of porous polymeric sorbent at 25° C. and 20 bar.

8. The method of claim 1, wherein an amount of carbon dioxide sorbed on the porous polymeric sorbent in mmoles/gram is at least 3 times greater at 25° C. and 20 bar than at 25° C. and 1 bar.

9. The method of claim 1, wherein sorbing occurs at a first pressure and the method further comprises removing carbon dioxide sorbed on the porous polymeric sorbent at a second pressure that is lower than the first pressure and that is greater than or equal to 1 bar.

10. The method of claim 1, wherein the gas mixture comprises carbon dioxide and methane and wherein an amount of carbon dioxide sorbed on the porous polymeric sorbent in mmoles/gram at 25° C. and 20 bar is at least 2 times greater than an amount of methane sorbed on the porous polymeric sorbent in mmoles/gram at 25° C. and 20 bar.

11. A composition comprising:
   (a) a porous polymeric sorbent having a BET specific surface area equal to at least 300 $m^2$/gram, the polymeric sorbent comprising
   (i) 8 to 52 weight percent of a first monomeric unit of Formula (I);

(I)

(ii) 48 to 85 weight percent of a second monomeric unit of Formula (II); and (II)

(iii) 0 to 20 weight percent of a third monomeric unit of Formula (III) wherein $R^1$ is hydrogen or alkyl; and (III)

(b) carbon dioxide sorbed on the porous polymeric sorbent.

12. The composition of claim 11, wherein the amount of carbon dioxide sorbed on the porous polymeric sorbent at 20 bar and 25° C. is at least 2 mmoles/gram.

13. The composition of claim 11, wherein the porous polymeric sorbent comprises (i) 8 to 40 weight percent of the first monomeric unit of Formula (I), (ii) 48 to 75 weight percent of the second monomeric unit of Formula (II), and (iii) 0 to 20 weight percent of the third monomeric unit of Formula (III).

14. The composition of claim 11, wherein the porous polymeric sorbent has a total pore volume of at least 0.25 cm³/gram, the total pore volume being measured by adsorbing argon at 77° K at a relative pressure equal to 0.98±0.01.

15. The composition of claim 11, wherein an amount of carbon dioxide sorbed on the porous polymeric sorbent in mmoles/gram is at least 3 times greater at 25° C. and 20 bar than at 25° C. and 1 bar.

* * * * *

UNITED STATES PATENT AND TRADEMARK OFFICE
CERTIFICATE OF CORRECTION

PATENT NO. : 10,058,844 B2
APPLICATION NO. : 15/580733
DATED : August 28, 2018
INVENTOR(S) : Wendland et al.

Page 1 of 1

It is certified that error appears in the above-identified patent and that said Letters Patent is hereby corrected as shown below:

In the Specification

Column 10
Line 59, delete "azobis(2-methylproprionate))," and
insert -- azobis(2-methylpropionate)), --, therefor.

Signed and Sealed this
Sixteenth Day of October, 2018

Andrei Iancu
*Director of the United States Patent and Trademark Office*